(12) United States Patent
Suh et al.

(10) Patent No.: US 6,245,907 B1
(45) Date of Patent: Jun. 12, 2001

(54) PROCESS FOR PRODUCING A HIGH PURITY CAPROLACTAM

(75) Inventors: Myung Suk Suh; Seung Eon Park; Chang Hwang Lee; Myeong Hong Lee, all of Seoul; Si Geun Lee, Kyoungki-do; Jung Ho Kim, Seoul, all of (KR)

(73) Assignee: Hyosung Corporation, Seoul (KR)

( * ) Notice: Subject to any disclaimer, the term of this patent is extended or adjusted under 35 U.S.C. 154(b) by 0 days.

(21) Appl. No.: 09/205,900

(22) Filed: Dec. 4, 1998

(30) Foreign Application Priority Data

Dec. 8, 1997 (KR) ................................................ 97-66783

(51) Int. Cl.⁷ .................................................. C07D 201/04
(52) U.S. Cl. ........................................... 540/534; 540/535
(58) Field of Search ...................................... 540/534, 535

(56) References Cited

U.S. PATENT DOCUMENTS

| 4,117,246 | 9/1978 | Plantema | 568/821 |
| 5,900,482 | * 5/1999 | Teramoto et al. | 540/535 |

FOREIGN PATENT DOCUMENTS

| 0552809 | 7/1993 | (EP) | C07C/5/11 |
| 1381149 | 1/1975 | (GB) | C07C/35/08 |
| 8193062 | * 7/1996 | (JP) | |
| WO97/03956 | 6/1997 | (WO) | |

* cited by examiner

*Primary Examiner*—Bruck Kifle
(74) *Attorney, Agent, or Firm*—Clark & Elbing LLP

(57) ABSTRACT

Disclosed is a process for producing a high purity caprolactam which comprises converting cyclohexene obtained by the partial hydrogenation of benzene into cyclohexanol through hydration, converting the cyclohexanol into cyclohexanone through dehydrogenation, converting the cyclohexanone into cyclohexanone oxime through oximation and converting the cyclohexanone oxime into caprolactam through the Beckman rearrangement, characterized by comprising isolating and purifying the methylcyclopentanol from the cyclohexanol prior to use of such cyclohexanol in dehydrogenation and feeding the isolated methylcyclopentanol directly to oximation in order that the methylcyclopentanol is not fed to dehydrogenation. The process of the invention advantageously provides an economic method for producing a caprolactam with greater purity.

13 Claims, 2 Drawing Sheets

PROCESS FOR PRODUCING A HIGH PURITY CAPROLACTAM

BACKGROUND OF THE INVENTION

1. Field of the Invention

The present invention relates to a process for producing a high purity caprolactam, and more particularly, to an efficient process for producing a high purity caprolactam, which comprises separating methylcyclopentanol contained in cyclohexanol prepared by the hydration of cyclohexene, which is obtained through partial hydrogenation of benzene, and removing efficiently methylcyclopentanone contained in cyclohexanone to be provided subsequently in oximation.

2. Description of the Prior Art

Cyclohexanone which is used in the manufacture of high purity caprolactam is prepared generally by dehydrogenation of cyclohexanol. The yield of this reaction depends on the various reaction conditions and a kind of a catalyst used, but in general is 40–90% of conversion at a temperature of from 100 to 400° C., and an atmospheric pressure of 0–10. At this reaction, the catalyst may be used in powder form or in particulate form, but a particulate form catalyst is more desirable so as to obtain a better result. In general, these catalysts are used alone without using a carrier, or in conjunction with a known carrier, if necessary.

On the other hand, the general process for producing cyclohexanol includes a process comprising oxidation of cyclohexane prepared by hydrogenation of benzene to provide a mixture of cyclohexanol and cyclohexanone and a process comprising converting benzene into cyclohexene through partial hydrogenation, and subsequent hydration of cyclohexene.

In the former process, the oxidation product of cyclohexane that is prepared in the form of a mixture of cyclohexanol and cyclohexanone is produced by oxidation of cyclohexane using a gas including a molecular oxygen as an oxidant in a liquid phase. In this response, conversion and selectivity may be controlled by using a supported or non-supported catalyst system. However, there is economic disadvantage in recovering cyclohexanol because of a low conversion of the reaction. In addition, the ratio of the resultant alcohol to ketone must be controlled carefully upon preparing a mixture of cyclohexanol and cyclohexanone obtained through oxidation of cyclohexane.

In common, the ratio of alcohol exceeds the ratio of ketone.

In the latter process, partial hydrogenation of benzene by using a transition metal catalyst and co-catalyst system in an aqueous solution phase produces cyclohexene which is then hydrated by the inorganic solid acid catalyst to provide cyclohexanol. Advantageously, the partial hydrogenation reaction is carried out in such a way that benzene is mainly converted into its main reaction product, cyclohexene, while production of cyclohexane, which is a byproduct of the reaction, is suppressed by contacting the benzene with hydrogen gas in the presence of any catalyst selected form the catalysts described hereinafter.

EP 552, 809 A1 discloses a particulate hydrogenation catalyst comprised mainly of metallic ruthenium, and more particularly, a mixture of a ruthenium catalyst using a zinc compound as its co-catalyst and an oxide or a hydroxide of a metal such as silica, alumina, zirconium, or hafnium or the like which is used as a dispersing agent for increasing selectivity and accomplishing stability of the catalyst. On the other hand, examples of a catalyst for hydration of cyclohexanol include an inorganic acid(British Patent Nos. 1,381,149 and 1,542,996), hetero polyacid(Japanese Patent Publication SHO 58-1089), organic acid(Japanese Patent Publication SHO 43-16125) or zeolite(Japanese Patent Publication SHO 194828), or the like. Out of the above-mentioned catalysts, zeolite is desirable because it can provide advantages such as separation of catalyst and product and suppression of a side reaction.

A process for producing cyclohexanone through a dehydrogenation of cyclohexanol is more advantageous as compared to a process for producing cyclohexanone through a dehydrogenation of a mixture of cyclohexanol and cyclohexanone prepared by an oxidation of cyclohexane in that it can provide savings in production cost and more stability in production process. Accordingly, much attention is paid to the former process.

In spite of the above-mentioned advantages, the process for the production of cyclohexanol by the partial hydrogenation of benzene and subsequent hydration of the cyclohexene has a drawback that leads to a formation of undesired impurities such as methylcyclopentanol, cyclohexylcyclohexene isomer, and dicyclohexyl ether in cyclohexanol. These impurities are produced in an amount of 0–1000 ppm according to process conditions and are known to be produced by an isomer reaction or a dimerization or an etherification reaction between the partial hydrogenation and hydration. Cyclohexyl-cyclohexene isomer and dicyclohexyl, out of the aforementioned impurities, are high-boiling point compounds, so they can be easily removed during the cyclohexanol dehydrogenation process or by a column for removing a high-boiling point compound and a low-boiling point compound which is provided in front of a distillation column for separating a mixture of cyclohexanol and cyclohexanone. In contrast, there is significant difficulty in removing the methylcyclopentanol because its boiling point is almost the same as that of the content of a reactor. In the case that the methylcyclopentanol is converted to methylcyclopentanone and is fed to an oximation process, a purity of caprolactams produced through a Beckmann rearrangement and the quality of an ammonium sulfate by-product will tend to be deteriorated.

As a method for overcoming these problems, International Patent Publication 97/WO03956(Japanese Patent No. 9031052) describes a process for the production of ε-caprolactam capable of reducing the methylcyclopentanone content of the cyclohexanone to be converted into the oxime to 400 ppm or less by providing an additional distillation column to a conventional distillation process or by adopting a strict distillation condition so as not to subject methylcyclopentanone to be fed subsequently in oximation. However, this process suffers from considerable technical shortcomings, since providing the additional distillation column and adopting the strict distillation condition entail high maintenance costs and operation costs. Moreover, the quality of a caprolactam produced by this process cannot meet the quality requirement since the methylcyclopentanone is not removed completely.

Thus, the present inventors have repeated studies in order to overcome the above problems encountered in the prior art, keeping in mind that the methylcyclopentanol contained in the cyclohexanol was converted to the methylcyclopentanone, and if the methylcyclopentanone was fed to oximation, it became difficult to remove and affected adversely the subsequent process and quality of the product, whereas methylcyclopentanol itself did not affect the subsequent process and quality of the product unlike methylcyclopentanone. Consequently, we discovered that removal of the methylcyclopentanol from the cyclohexanol prior to use of such cyclohexanol in dehydrogenation so as not to form methylcyclopentanone through dehydrogenation improves the overall efficiency of the process and quality of the caprolactam.

SUMMARY OF THE INVENTION

Therefore, it is an object of the invention to overcome the problems encountered in the prior art and to provide a process for producing a high purity caprolactam which is easy to carry out industrially and produces only very small amounts of impurities which are difficult to remove.

We found that the above object is achieved by a process for producing a high purity caprolactam which comprises converting cyclohexene obtained by a partial hydrogenation of benzene into cyclohexanol through hydration, converting the cyclohexanol into cyclohexanone through dehydrogenation, converting the cyclohexanone into of cyclohexanone oxime through oximation and converting the cyclohexanone oxime into caprolactam through a Beckman rearrangement, characterized by comprising isolating and purifying the methylcyclopentanol from the cyclohexanol prior to use of such cyclohexanol in subsequent dehydrogenation and feeding the isolated methylcyclopentanol directly to oximation without passing dehydrogenation.

BRIEF DESCRIPTION OF THE DRAWINGS

Other objects and aspects of the invention will become apparent from the following description of embodiments with reference to the accompanying drawings in which.

DESCRIPTION OF THE PREFERRED EMBODIMENTS

The term "methylcyclopentanol", when used herein, includes 1-methylcyclopentanol, 2-methylcyclopentanol and 3-methylcyclopentanol. As a rule, the boiling points of cyclohexanol, cyclohexanone, methylcyclopentanol isomer, and methylcyclopentanone isomer are 161° C., 155° C., 136–152° C., and 139–145° C., respectively. These differences in boiling points are utilized as an important motive in the present invention.

Figure 1:
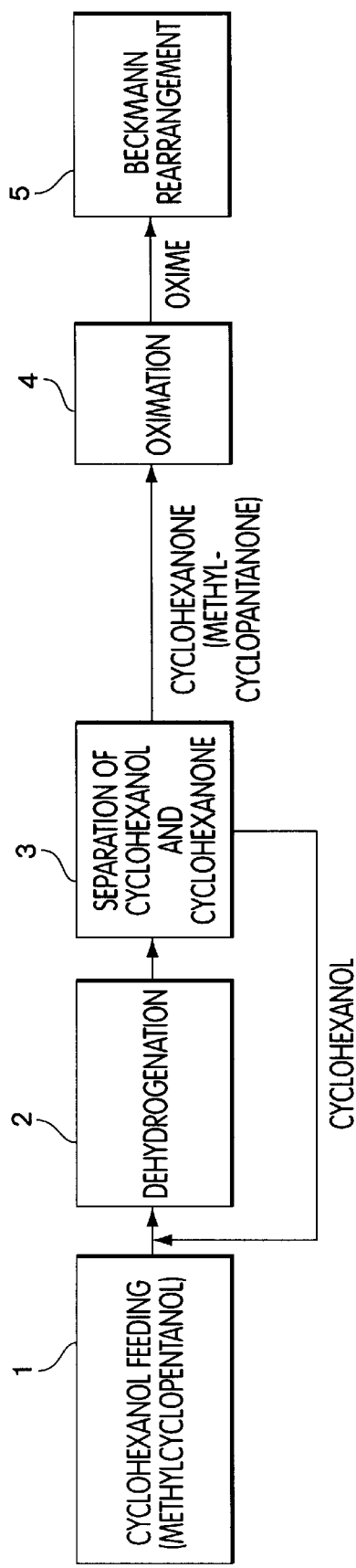
FIG. 1 is a schematic drawing of a conventional method for producing caprolactam.

FIG. 1 illustrates a conventional method for producing caprolactam, wherein cyclohexanol 1 starting material is fed just before dehydrogenation 2, and then converted to a mixture of cyclohexanol and cyclohexanone through dehydrogenation. The resulting reaction mixture is then separated into high-boiling point cyclohexanol and low-boiling point cyclohexanone through fractional distillation 3. The high-boiling point cyclohexanol flows downwardly into a lower portion of a distillation column, whereas the low-boiling point cyclohexanone is vaporized upwardly to an upper portion of the column and is separated. The cyclohexanol which is recovered in a lower portion of a distillation column is recycled back to the first reaction process and is fed to the dehydrogenation 2. At this time, methylcyclopentanol-based impurities contained in the cyclohexanol are converted into methylcyclopentanone via dehydrogenation, and then are provided to oximation in conjunction with the cyclohexanone. As a result, in this prior art process, it is not possible to obtain a high purity caprolactam due to the methylcyclopentanol-based impurities. In order to overcome this problem, one can provide an additional distillation column to the entire reaction system or recover a mixture of cyclohexanol and cyclohexanone at a strict distillation condition so as to prevent methylcyclopentanone from being fed to oximation process. However, this method may result in a substantial increase in production cost.

Figure 2:
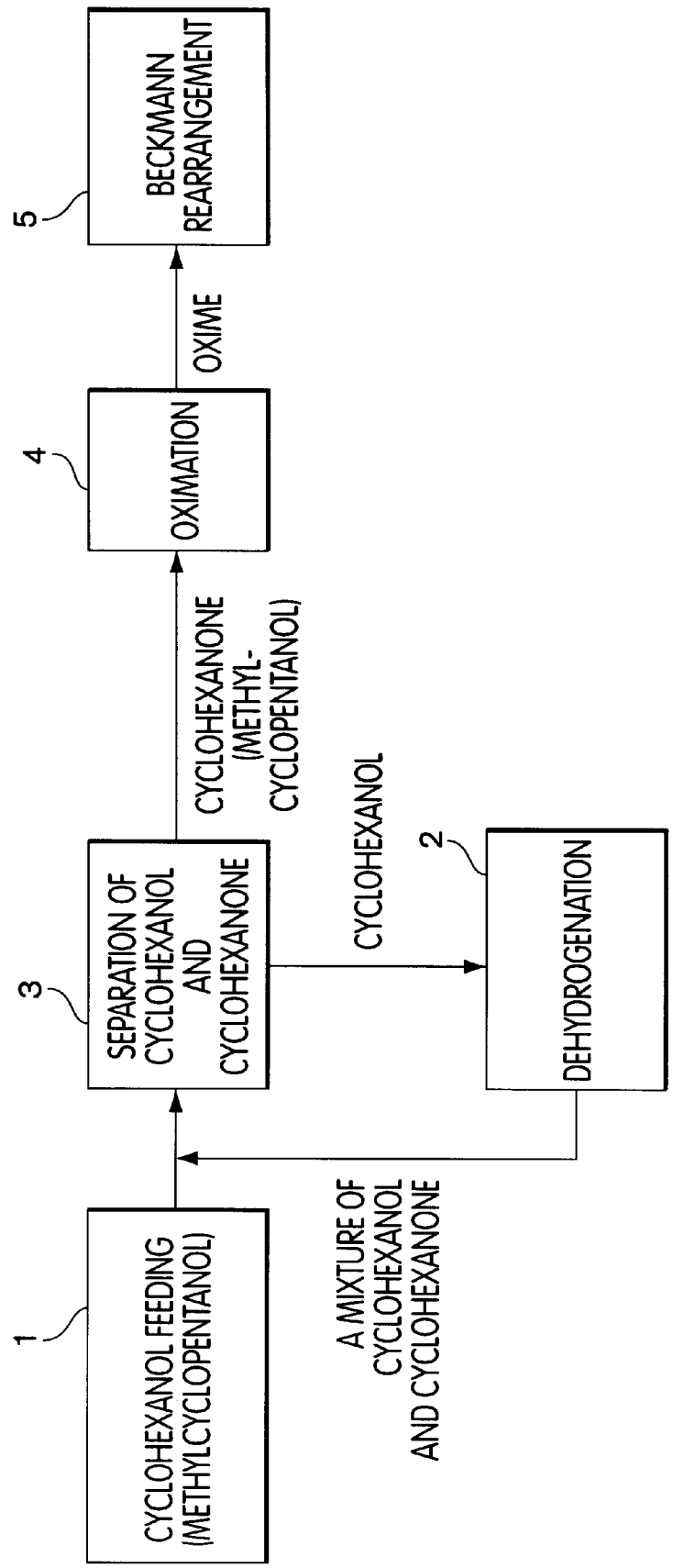
FIG. 2 is a schematic drawing of a process for producing a high purity caprolactam according to the present invention.

As shown in FIG. 2, the present invention is featured by feeding of cyclohexanol 1 carried out posterior to dehydrogenation 2 and just prior to separation of the cyclohexanol and cyclohexanone 3.

In the separation process of the cyclohexanol and the cyclohexanone 3 of the invention, cyclohexanol which is added in the cyclohexanol feeding process 1 and a mixture of cyclohexanol and cyclohexanone returned from the preceding dehydrogenation process 2 are subjected to fractional distillation. At this process, the cyclohexanone with a low boiling point is vaporized toward an upper part of the distillation column, and then fed to oximation, whereas the cyclohexanol with a high boiling point is provided to dehydrogenation 2 in a liquid phase.

The cyclohexanol to be fed to a separation process 3 from the cyclohexanol feeding process 1 includes methylcyclopentanol derivatives. These derivatives are mostly vaporized in conjunction with cyclohexanone, and to be introduced, not to dehydrogenation 2, but to oximation 3 since they have a lower boiling point as compared to the cyclohexanol. This alcohol compound does not perform oxination with hydroxylamine and does not affect the subsequent processes.

Therefore, the methylcyclopentanol is not introduced in the dehydrogenation 2 or if any, only 400 ppm or less of the cyclohexanol is introduced. At this process, the reactants are converted to a mixture of cyclohexanone and unreacted cyclohexanol at the conversion of 40–70%. The mixture of the cyclohexanone and the cyclohexanol passing through dehydrogenation 2 is mixed with a newly added cyclohexanol comprising methylcyclopentanol impurities, and then is introduced to the separation process 3. The dehydrogenation 2 is desirable to be carried out in the presence of Fe/ZnO or copper/silica mixture catalyst.

The separation process 3 of the cyclohexanol and cyclohexanone may be carried out under various pressures. Preferably, the process is performed under an atmospheric pressure of 10–760 mmHg, more preferably, 30–70 mmHg. In the present invention, a distillation column consists of 50 to 100 stages.

An additional distillation column can be provided before and after the separation process 3 of the cyclohexanol and cyclohexanone under reduced pressure or the ordinary atmospheric pressure in order to remove a low-boiling point compound (for example, water and hydrocarbon derivatives of 6–9 carbons) and a high-boiling point compound (dicyclohexyl ether, cyclohexylcyclohexene, phenol and other high-boiling point compound). Controlling of temperature and atmospheric pressure upon installing the additional distillation column depends largely on a composition of a reactant. In general, the low-boiling point compound is separated at a pressure of 100–760 mmHg, while the high-boiling point compound is separated at a pressure of 10–100 mmHg. Separation is carried out at the optimum condition that allows the distillation cost to be minimum.

The above-mentioned cyclohexanone without methylcyclopentanone is converted to cyclohexanone oxime through oximation 4. This reaction is carried out by a reaction of cyclohexanone with hydroxylamine, wherein the hydroxylamine is preferably utilized in the form of a sulfate salt or a hydrochloric acid salt since it is not stable under ordinary conditions. For example, the cyclohexanone is reacted with the hydroxylamine sulfate in the aqueous solution phase or non-aqueous solution phase. The oximation for producing cyclohexanone oxime can be carried out by any known method which is suitable for this purpose. For example, the oximation may be carried out by reacting cyclohexanone with nitrogen monoxide and hydrogen in the presence of a noble metal catalyst or by reacting cyclohexanone with ammonia in the presence of hydrogen peroxide.

Finally, the resulting cyclohexanone oxime is converted into caprolactam by Beckmann rearrangement 5.

The Beckmann rearrangement 5 is carried out by reacting cyclohexanone oxime with oleum or concentrated sulfuric acid at a suitable temperature, and then followed by neutralization with a basic compound such as aqueous ammonia to give a crude caprolactam. In case that the cyclohexanone oxime is converted in the presence of oleum, the ratio of sulfuric acid to cyclohexanone oxime is preferably 1.0–2.0, by mole ratio. At this process, oleum is more useful than sulfuric acid, and as a rule, the oleum having an $SO_3$ content of 10–30% by weight is used. The Beckmann rearrangement of cyclohexanone oxime with oleum is desirably performed at a temperature from 60° C. to 100° C. At low temperature, side reaction is suppressed, but a viscosity of a reactant is increased, and the reverse phenomena occur at a high temperature, so the temperature has to be controlled carefully considering a yield and efficiency of the process. Cooling is needed in Beckmann rearrangement so as to remove the heat of the reaction.

In the present invention, advantageously a ruthenium catalyst is used in hydrogenation of benzene, and a solid acid catalyst is used in hydration of cyclohexene.

The crude caprolactam obtained by the Beckmann rearrangement can be separated and purified by any suitable method, such as, for example, extraction by an organic solvent and subsequent distillation under reduced pressure to provide caprolactam. The process for producing a high purity caprolactam according to the present invention may be carried out on a batch basis or continuously.

Although the preferred embodiments of the invention have been disclosed for illustrative purposes, those skilled in the art will appreciate that various modifications, additions and substitutions are possible, without departing from the scope and spirit of the invention as disclosed in the accompanying claims. In the following examples, a composition of a solution is analyzed quantitatively by a gas chromatography using a capillary column.

EXAMPLE 1

400 ppm of methylcyclopentanol was added to 500 g of cyclohexanol without a methylcyclopentanol and a methylcyclopentanone, and then 500 g of cyclohexanone was added thereto. The resulting mixture of cyclohexanol and cyclohexanone was separated according to the separation process 3 of a method depicted in FIG. 2 to provide cyclohexanol. The above separation was carried out in a distillation column, wherein a temperature of an upper stage of the distillation column was set to 73° C. and the first stage comprised of 30 stages of distillation stages, the second stage comprised of 20 stages and the third stage comprised 30 stages. The purity of the purified cyclohexanone was 99.6%, and methylcyclopentanol content of cyclohexanone was 380 ppm, and methylcyclopentanol content of cyclohexanol was less than 20 ppm.

EXAMPLE 2

A cyclohexanol was prepared by the same method described in example 1 except that 800 g of methylcyclopentanol was added. The purity of the purified cyclohexanone was 99.5%, and methylcyclopentanol content of cyclohexanone was 770 ppm, and methylcyclopentanol content of cyclohexanol was less than 30 ppm.

EXAMPLE 3

A cyclohexanol was prepared by the same method described in example 1 except that 1200 ppm of methylcyclopentanol was added. The purity of the purified cyclohexanone was 99.6%, and methylcyclopentanol content of cyclohexanone was 1150 ppm, and methylcyclopentanol content of cyclohexanol was less than 40 ppm.

EXAMPLE 4

400 ppm of methylcyclopentanol was added to a 500 g of cyclohexanol without a methylcyclopentanol to be fed newly, and then a mixture solution of the cyclohexanol and the cyclohexanone which is prepared by dehydrogenation of 1000 g of cyclohexanol without methylcyclopentanol was added thereto. Thereafter, a cyclohexanone was purified by the same method as Example 1. The dehydrogenation was carried out in a gas phase by vaporizing cyclohexanol in the presence of a catalyst via pretreating and activating in a reactor. After completion of the dehydrogenation, the resulting mixture solution of the cyclohexanol and the cyclohexanone was introduced to a separation process. The dehydrogenation process was proceeded by using a copper/silica as catalyst under the condition of a temperature of 240° C. and a pressure of 760 mmHg. LHSV(Liquid Hourly Space Velocity) was 0.7 l/g cat.hr. The LHSV was mainly controlled by controlling a flow rate of an inlet of a reactor and a conversion of the reaction was 50%. The purity of the purified cyclohexanone was 99.7%, and methylcyclopentanol content of cyclohexanone was 390 ppm, and methylcyclopentanol content of cyclohexanol was less than 10 ppm.

EXAMPLE 5

A cyclohexanol was prepared by the same method described in example 4 except that 800 ppm of methylcyclopentanol was added. The purity of the purified cyclohexanone was 99.5%, and methylcyclopentanol content of cyclohexanone was 780 ppm, and methylcyclopentanol content of cyclohexanol was less than 10 ppm.

EXAMPLE 6

A cyclohexanol was prepared by the same method described in example 4 except that 1200 ppm of methylcyclopentanol was added. The purity of the purified cyclohexanone was 99.6%, and methylcyclopentanol content of cyclohexanone was 1160 ppm, and methylcyclopentanol content of cyclohexanol was less than 15 ppm.

EXAMPLE 7

200 g of cyclohexanone obtained in the example 4 and 20% aqueous ammonia solution were simultaneously added dropwise to a 20% aqueous solution of hydroxylamine sulfate, while keeping pH 4–4.5, and then an additional large amount of hydroxylamine was added thereto and reacted for an additional 30 minutes. An oil layer was removed and then dehydrated under reduced pressure to give cyclohexanone oxime.

The resulting cyclohexanone oxime and 25% oleum (1.5 equivalents based on sulfuric acid) were introduced in a reactor for the Beckmann rearrangement at 80–100° C. for 1 hour. Cooling was performed so as to suppress a local heating. The resulting mixture was neutralized with a 10% by weight aqueous ammonia to give a caprolactam reactant, while adjusting a reaction condition of pH 6–7 and a temperature of 70–80° C.

The resulting neutralized solution was extracted with toluene three times in a separatory funnel. At this stage, a concentration of caprolactam contained in toluene has to be kept so as not to exceed 20%. The resulting organic layer was removed and distilled under reduced pressure so as to remove the toluene and minor amounts of moisture content to give a crude caprolactam. Thereafter, a suitable amount of a sodium hydroxide was added to the crude caprolactam, and then the resulting product was purified by distillation under a high vacuum to provide 3-parts caprolactams comprised of 10% of the first part, 70% of the middle part and 20% of the remainder. The caprolactam of the middle part was considered as a purified caprolactam and its purity was analyzed. For the purified caprolactam, PZ and volatile bases were determined and the results obtained were shown in Table 1.

EXAMPLE 8

A purified caprolactam was prepared by the same method described in example 7 except that 200 g of cyclohexanone which is obtained in example 5 was added. For the purified caprolactam, PZ and volatile bases were determined and the results obtained were shown in Table 1.

EXAMPLE 9

A purified caprolactam was prepared by the same method described in example 7 except that 200 g of cyclohexanone which is obtained in example 6 was added. For the purified caprolactam, PZ and volatile bases were determined and the results obtained were shown in Table 1.

TABLE 1

|  | Example 7 | Example 8 | Example 9 |
|---|---|---|---|
| Pz | 15300 | 13100 | 12800 |
| Volatile bases | 0.6 | 0.6 | 0.7 |

[TEST METHOD]

PZ(Permanganate-zahl: a Number of Permanganate:

To determine the PZ, 1 g of a caprolactam sample was dissolved in 100 ml of water and treated with 1 ml of aqueous solution of 0.01 N potassium permanganate. Thereafter, the time period was determined on a second basis that it takes until a color of a reaction solution became the same as that of standard solution due to an oxidizable material.

Volatile Bases [mEq/kg]:

To determine the Volatile bases, 30 g of caprolactam was dissolved in 400 ml aqueous solution of a sodium hydroxide. After boiling the resulting product for 1 hour, the producing decomposition gas and distilled water were added in 500 ml of deionized water which is prepared by dissolving 4 ml of a 0.02 N aqueous solution of hydrochloric acid therein, followed by titrating with a 0.1 N sodium hydroxide. The volatile bases are equivalent to the value that a reduced portion of a hydrochloric acid is converted to a value for ammonia.

COMPARATIVE EXAMPLE 1

In order to illustrate the effects of the present invention as compared to a conventional process for producing caprolactam, cyclohexanone was purified by the method depicted in FIG. 1. 400 ppm of methylcyclopentanol was added to 500 g of cyclohexanol free of methylcyclopentanol and methylcyclopentanone and the dehydrogenation process of Example 4 was repeated. The mixture of the cyclohexanol and the cyclohexanone obtained by the preceding dehydrogenation was separated by the same method as Example 1. The conversion of cyclohexanone was 53%, and the purity of the cyclohexanone obtained was 99.4%, and methylcyclopentanone content of cyclohexanone was 610 ppm, and methylcyclopentanol content of cyclohexanol was less than 10 ppm.

COMPARATIVE EXAMPLE 2

The cyclohexanone was purified by the same method described in comparative example 1 except that 800 ppm of methylcyclopentanol was added. The conversion of cyclohexanone was 49%, and the purity of the cyclohexanone obtained was 99.4%, and methylcyclopentanone content of cyclohexanone was 1275 ppm, and methylcyclopentanol content of cyclohexanol was less than 15 ppm.

COMPARATIVE EXAMPLE 3

The cyclohexanone was purified by the same method described in comparative example 1 except that 1200 ppm of methylcyclopentanol was added. The conversion of cyclohexanone was 55%, and the purity of the cyclohexanone obtained was 99.4%, and methylcyclopentanone content of cyclohexanone was 1970 ppm, and methylcyclopentanol content of cyclohexanol was less than 20 ppm.

The results obtained in examples 1–6 and comparative examples 1–3 were shown in Table 2.

TABLE 2

|  | A | B | C | D |
|---|---|---|---|---|
| EXAMPLE 1 | 400 | 380 | <20 | — |
| EXAMPLE 2 | 800 | 770 | <30 | — |
| EXAMPLE 3 | 1200 | 1150 | <40 | — |
| EXAMPLE 4 | 400 | 390 | <10 | — |
| EXAMPLE 5 | 800 | 780 | <10 | — |
| EXAMPLE 6 | 1200 | 1160 | <15 | — |
| Comparative Example 1 | 400 | — | <10 | 610 |
| Comparative Example 2 | 800 | — | <15 | 1275 |
| Comparative Example 3 | 1200 | — | <20 | 1970 |

A: An amount of methylcyclopentanol added (ppm)
B: Methylcyclopentanol content of cyclohexanone (ppm)
C: Methylcyclopentanol content of cyclohexanol (ppm)
D: Methylcyclopentanone content of cyclohexanone (ppm)

As can be seen from Table 2, according to the present invention, the methylcyclopentanol which is contained in the cyclohexanol as an impurity may be readily removed and not provided to a dehydrogenation process, thereby little methylcyclopentanone which affects adversely to oximation is produced. As a result, the purified cyclohexanone free of methylcyclopentanone impurity is fed to the subsequent process. Accordingly, the novel process has the advantage that quality of the caprolactam is substantially improved and the production cost is reduced.

What is claimed is:

1. A process for producing a high purity caprolactam, comprising:

(a) providing a mixture comprising cyclohexanol, cyclohexanone and methylcyclopentanol, and subjecting the mixture to a separation process capable of fractionating cyclohexanol and cyclohexanone, to yield a first fraction comprising cyclohexanol that is substantially free of methylcyclopentanol and a second fraction that comprises cyclohexanone and methylcyclopentanol;

(b) treating the first fraction of step (a) to convert a portion of the cyclohexanol into cyclohexanone through dehydrogenation, to yield a mixture of cyclohexanol and cyclohexanone that is substantially free of methylcyclopentanone;

(c) subjecting the cyclohexanol/cyclohexanone mixture of step (b) to the separation process of step (a) and combining the resultant cyclohexanone-containing fraction with the cyclohexanone-containing fraction of step (a);

(d) converting the cyclohexanone-containing fraction of step (c) into cyclohexanone oxime through oximation, such that the methylcyclopentanol contained in the cyclohexanone is not subjected to dehydrogenation or oximation; and (e) converting the cyclohexanone oxime of step (d) into caprolactam through Beckman rearrangement.

2. The method of claim 1, wherein the cyclohexanol and methylcyclopentanol provided in step (a) is obtained by converting cyclohexene, obtained by the partial hydrogenation of benzene, into cyclohexanol through hydration, wherein said cyclohexanol contains methylcyclopentanol.

3. A process as claimed in claim 2, wherein said partial hydrogenation of benzene is effected by using a ruthenium catalyst.

4. A process as claimed in claim 2, wherein said hydration of cyclohexene is effected by using a solid acid catalyst.

5. A process as claimed in claim 1, wherein said dehydrogenation of cyclohexanol is effected by using a copper compound or Fe/ZnO catalyst.

6. A process as claimed in claim 1, wherein said oximation is effected by reacting cyclohexanone with hydroxylamine.

7. A process as claimed in claim 1, wherein said Beckmann rearrangement is effected by rearranging cyclohexanone oxime in the presence of a sulfuric acid or oleum.

8. The method of claim 1, wherein methylcyclopentanol concentrations in the first fraction of step (a) are less than about 40 ppm.

9. The method of claim 1, wherein methylcyclopentanol concentrations in the first fraction of step (a) are less than about 20 ppm.

10. The method of claim 1, wherein methylcyclopentanol concentrations in the first fraction of step (a) are less than about 10 ppm.

11. The method of claim 1, wherein at least about 95% of methylcyclopentanol fractionates with cyclohexanone in step (a).

12. A process for preparing a caprolactam from cyclohexene comprising the steps of:

hydration of cyclohexene to form cyclohexanol, conversion of cyclohexanol into cyclohexanone by dehydration, separation of cyclohexanol from cyclohexanone, formation of cyclohexanone oxime by reaction of cyclohexanone with a hydroxylamine, and formation of caprolactam by Beckman rearrangement, the process characterized in that, distillation separation of methylcyclopentanol impurities from cyclohexanol and cyclohexanone takes place prior to dehydrogenation of the mixture such that methylcyclopentanol fractionates with the cyclohexanone and is, therefore, not subject to dehydrogenation.

13. The method of claim 12, wherein at least 95% of the methyl cyclopentanol fractionates with the cyclohexanone.

* * * * *

UNITED STATES PATENT AND TRADEMARK OFFICE
CERTIFICATE OF CORRECTION

PATENT NO. : 6,245,907 B1
DATED : June 12, 2001
INVENTOR(S) : Myung Suk Suh, Seung Eon Park, Chang Hwang Lee, Myeong Hong Lee, Si Geun Lee and Jung Ho Kim It is certified that error appears in the above-identified patent and that said Letters Patent is hereby corrected as shown below:

Column 1,
Line 6, replace "1. Field of the Invention" with -- Field of the Invention --;
Line 15, replace "2. Description of the Prior Art" with -- Description of the Prior Art --;

Column 4,
Line 27, replace "oxination" with -- oximation --;

Column 5,
Lines 11 and 12, join "into caprolactam by Beckmann rearrangement 5." with
-- into caprolactam by Beckmann rearrangement 5. The Beckmann rearrangement
5 is carried out by reacting --;
Line 23, replace "At low temperature," with -- At a low temperature, --; and Column 7,
Line 40, replace "Pz" with -- PZ --.

Signed and Sealed this

Sixth Day of August, 2002

Attest:

Attesting Officer

JAMES E. ROGAN
Director of the United States Patent and Trademark Office